United States Patent [19]

Jelenko, III

[11] 4,025,645

[45] May 24, 1977

[54] NON-STEROID TOPICAL AGENT FOR ALLEVIATING INFLAMMATION IN MAMMALS

[76] Inventor: Carl Jelenko, III, 2716 Wellington Drive, Augusta, Ga. 30904

[22] Filed: Jan. 27, 1976

[21] Appl. No.: 652,670

[52] U.S. Cl. .............................................. 424/312
[51] Int. Cl.² ....................................... A61K 31/23
[58] Field of Search ................................... 424/312

[56] References Cited

UNITED STATES PATENTS

| | | | |
|---|---|---|---|
| 3,676,472 | 7/1972 | Zilliker | 424/312 |
| 3,920,848 | 11/1975 | Jelenko | 424/312 |

Primary Examiner—Stanley J. Friedman
Attorney, Agent, or Firm—John S. Roberts, Jr.

[57] ABSTRACT

The present invention is a method of treating mammals for alleviating inflammation by utilization of a non-steroid topical agent. The agent is ethyl linoleate [ethyl-cis,cis(9,12)-octadecadienoate] which may be combined in a preferred formulation with one or more antioxidants such as $\alpha$-tocopherol, d,l-histidine, and tertiary butyl hydroquinone; a stabilizer such as Tween-80; and inert esters such as ethyl oleate, ethyl palmitate, and ethyl stearate. The agent is applied in a therapeutic dosage range of 0.2–0.8 mg/cm² of body surface both internal and external, with a preferred dosage of 0.5 mg/cm². This topical remedy for inflammation for internal and external body surfaces is utilized principally in a single dose but may be utilized in multiple doses are required due to low toxicity (60:1). Among the conditions with inflammatory responses amenable to treatment are ultraviolet ratiation, solar radiation, non-infectious conjunctivitis, hemorrhoids (acute), abrasions, ingrown finger or toenail (granulation), skin graft donor sites, vaginitis, poison ivy, psoriasis, herpes simplex (cold sores, aphthous ulcers), pruritis ani/cruri, chemical inflammation, and insect stings/bites.

13 Claims, No Drawings

NON-STEROID TOPICAL AGENT FOR ALLEVIATING INFLAMMATION IN MAMMALS

The present invention illustrates a new use for the known natural lipid ethyl linoleate [ethyl-cis,cis(9,12)-octadecadienoate]. This compound, with adequate food grade antioxidants or stabilizers, has been previously utilized in burn therapy to diminish water loss through the skin with a critical limitation of use with 12-hour post burn. Confer the following literature articles:

Jelenko, et al, "Studies in Burns. X. Ethyl Linoleate: The Water-Holding Lipid of Skin. A. The Evidence,"-*The Journal of Trauma*, 12:968–973 (1972).

Jelenko et al, "Studies in Burns. XI. Ethyl Linoleate: The Water-Holding Lipid of Skin. B. Effects on In Vivo Burn Eschar,"*The Journal of Trauma*, 12:974–978 (1972).

Jelenko et al, "Studies in Burns. XII. Evaporative Water Loss is Related to Postburn Hypermetabolism," *Journal of Surgical Research*, 16:498–503 (1974).

Additionally, in a further development in U.S. Pat. No. 3,920,848 Jelenko, the same compound is utilized as a topical agent for alleviation of full-thickness burns in mammals and a related application, Ser. No. 628,143 filed Nov. 3, 1975, shows a topical veterinary dermatological medicament using the same compound.

Outside of the inventor's own work, U.S. Pat. No. 3,676,472 Zilliken et al mentions the utilization of the methyl ester in vegetable oil for prophylactic effects in animals against Staphylococcus aureus but the protection by prophylactic dosage against bacteria and viral disease is foreign to the present application.

The preferred formulation for utilizing ethyl linoleate, EL, is designated h$\overline{EL}$ate™ and is as follows:

|  | Grams |
| --- | --- |
| Active Ingredient: |  |
| Ethyl linoleate | 35.95 |
| Anti-oxidants: |  |
| α-tocopherol | 0.43 |
| d,1-histidine | 0.78 |
| Tertiary butyl hydroquinone | 0.0002 |
| Stabilizer: |  |
| Tween-80 | 0.1539 |
| Inactive Ingredients: |  |
| Ethyl oleate | 10.07 |
| Ethyl palmitate and ethyl stearate, each | 1.92 |

The present invention, in contrast to the above known uses for ethyl linoleate, can be differentiated. The present invention relates to the alleviation of inflammatory response by topical application to body surfaces both external and internal. Inflammation can be defined broadly as "the reaction of irritated and damaged tissues which still maintain vitality: (Menaker, *Biologic Basis of Wound Healing*, Harper & Rowe, Hagerstown, MD, 1975, pages 42–63, 131–142, 258–290). Dunphy et al, *Wound Healing*, MEDCOM, Pearl River, NY, 1971, clearly distinguishes between the inflammatory phase of wound healing (page 20) and other phases of the process of healing. The inflammatory phase is also called the substrate phase and comprises vascular, hemostatic and cellular components which give rise to classic signs of inflammation (Menaker, ante, page 43) such as rubor (redness), calor (heat), dolor (pain), tumor (swelling), and functio laesa (altered function). This inflammatory phase is further described in Sabiston, *Textbook of Surgery*, W. B. Saunders Co., Philadelphia, PA, 1972, page 250, and is distinguished from healing per se.

Alternatively stated, inflammation, then, comprises a sequence of events during which there are changes in the small arterioles, the capillary and the postcapillary vessels such that fluid within the blood vessels escapes into the injured area along with certain cellular elements from within the blood stream. The blood vessels dilate and later plug. White blood cells move into the wound and ingest bacteria or other particulate foreign matter in the wound. Simultaneously, certain chemical materials are released within the wound and/or from other areas of the body. These materials include histamine, serotonin, and the prostaglandins (cf Menaker, ante, pages 260, 267–268) and in this application it is a function of the ethyl linoleate to alleviate or reduce the effect of these materials.

Interrelated with inflammation is the general topic of healing, which is defined by Sabiton (ante) as a "highly dynamic, integrated series of cellular, physiologic, and biochemical events which occur exclusively in whole organisms" and the end result is epithelialization, wound contraction, connective tissue repair, and wound remodeling (cf Dunphy, ante, page 22). It is necessary and a characteristic of healing that scar occurs (cf Dunphy et al, *Repair and Regeneration*, McGraw-Hill, New York, 1969, page 151). It should be noted that healing cannot occur without inflammation having occurred first. However, it does not follow that, because there is inflammation, there will be healing. Indeed, certain substances such as cortisone inhibit the initial inflammatory response and, hence, inhibit healing (cf Dunphy et al, *Wound Healing*, ante, page 11).

Regeneration is the "capacity to replace a missing part or structure but not the entire body" (cf Menaker, ante, page 293). Regeneration differs from wound healing in that the latter comprises the ability to close a lesion by the formation of scar and the covering epithelium and the former comprises total reorganization of the cells into tissues which are specifically organized into an organ of such complexity as a limb (cf Menaker, ante, page 293).

Healing, then, is a complex biophysical-chemical-physiological process in which, in response to dissolution of tissue integrity, a complex series of processes occurs which comprises the elaboration of chemical mediators, the alteration of local physiology (the inflammatory phase), and culminating with the laying down of scar and the covering of the area with an appropriate epithelium. Inflammation, then, must be a part of healing, but it can also exist by itself and not culminate in the establishment of contracted wound or the laying down of scar tissue. Furthermore, the elimination of inflammatory response results in a wound which may not heal and in which scar tissue may not be formed.

As above noted, certain of the characteristics of inflammation are mediated by such chemicals as serotonin, histamine, and the prostaglandins, and inhibition of the production of these materials will result in a wound which does not exhibit the inflammatory response. If this inhibition is adduced by cortisone drugs, wound healing may well be inhibited. In sharp and marked contrast, however, the use of ethyl linoleate eliminates the inflammatory response and sharply increases the rate of wound healing. In this case [i.e., where ethyl linoleate or h$\overline{EL}$ate™) is used] the wound closes and epithelializes, but contracture and scar formation does not occur. Therefore, hĒLate ™ acts as a non-steroid anti-inflammatory agent. Healing is not necessarily an outcome of the inflammation-reducing effect; and in those cases where wounds do in fact close and epithelialize, they do this by local regeneration rather than by healing.

Examples of inflammatory conditions favorably treated with ethyl linoleate are as follows: ultraviolet radiation, solar radiation, non-infectious conjunctivitis, hemorrhoids (acute), abrasions, ingrown finger or toenail (granulation), skin graft donor sites, vaginitis, poison ivy, psoriasis, herpes simplex (cold sores, aphthous ulcers), pruritis ani/cruri, chemical inflammation and insect stings/bites.

The present invention comprises the use of ethyl linoleate (hĒLate™) as a non-steroid anti-inflammatory agent in a variety of conditions. The commonality in these conditions comprises the fact that all represent inflammatory processes.

The causative agents of the various conditions are varied, ranging from irradiation to physical trauma, cellular over-proliferation, and contact with toxic agents. The commonality in therapy comprises as a preferred regimen a single topical application of ethyl linoleate. Commonality in response of the disease/injury process comprises abrupt and virtually instantaneous reversal of the inflammatory process.

In summation, as a modus of action of ethyl-cis,-cis(9,12)-octadecadienoate (hĒLate™), it is believed that these disparate conditions in the inflammatory process as exemplified by redness, swelling, edema, hyperemia, hypersensitivity (pain or itching) and/or exudation evidently are derived from signs and symptons caused by the release of serotonin into the wound and by histamine effects both locally and systemically. It is believed that the topical application of ethyl linoleate to the local lesion effects its beneficial office by interfering with the local production of these materials. It is further believed that this occurs through altered production of prostaglandin E. It is noted that the active ingredient of hĒLate™, ethyl linoleate [ethyl-cis,-cis(9,12)-octadecadienoate], is, chemically, extraordinarily similar to the natural precursor of prostaglandin E. The prostaglandins consist basically of a $C_{20}$ acid (prostanoic acid) containing a five-membered ring (cf Goodman and Gilman, *The Pharmacological Basis of Therapeutics*, 4th ed, MacMillan, 1970, pages 672–674). From the relationship of the compounds it is believed that ethyl linoleate acts as a competitive inhibitor to the production of prostaglandin and thereby blocks the histamine/serotonin response.

DOSAGE

The dosage recommended as to the active ingredient ethyl linoleate is a topical application of 15 mg/kg to 75 mg/kg with a preferred dosage of 25 mg/kg, where the kilogram unit refers to body weight of the mammal. This preferred dosage may be repeated as needed at the end of 5–7 days after initial dose. An alternative modus of expressing dosage is 0.2–0.8 mg/cm² of body surface both internal and external, with a preferred dosage of 0.5 mg/cm². A second method of expressing dosage based on skin coverage is a preferred level of from 1 drop (6.7 mg) per 16 in.² to 1 drop per 36 in.² based upon hairless skin. Additionally, to effectively treat small conditions, the dosage may be 1 drop for any area up to 36 in.²

In the discussion of dosage, it is noted that, whereas the recommended dosage is a single dose, there are cases where a second dose at an interval of 5–7 days is recommended and, since the margin of safety for toxicity is large and is about 60:1 of the recommended initial dose of 25 mg/kg of body weight, it is possible to utilize successive-day treatments and even multiple treatments per diem for small lesions (0.1–3% body surface area) at slightly lower unit dosages where deemed necessary with safety and freedom from side effects.

ANTIOXIDANTS

Anitoxidant additives include those found in a preferred composition set out in the Investigational New Drug Application before the Food and Drug Administration as follows:

α-tocopherol
d,l-histidine
Tertiary butyl hydroquinone (which is TBHQ)

Operable antioxidants also include those which are set out additionally in Kirk-Othmer II, volume 2, pages 593–597, outlining food grade antioxidants permitted in the United States and other countries. Such antioxidants are primarily inhibitors and the preferred group are tocopherols, propyl gallate, and norhydroguaiaretic acid (which is NDGA). These food grade antioxdants mentioned in Kirk-Othmer are incorporated by reference and made a part of this application. A similar list, which is also incorporated by reference, appears in Ralph G. Harry, *The Principles and Practice of Modern Cosmetics*, Volume 1, Modern Cosmeticology, page 617, 1962, and is reprinted below:

Guaiacum resin
Nordihydroguaiaretic acid
Tocopherols
Lecithin
Butylated hydroxyanisole
Butylated hydroxytoluene
Trihydroxybutyrophenone
Ascorbic palmitate
Monoisopropyl citrate
Thiodipropionic acid
Dilauryl thiodipropionate
Distearyl thiodipropionate In the above formulation, in addition to the antioxidants, it is noted that the active ingredient is ethyl linoleate isomer and that certain inert esters (ethyl oleate, ethyl palmitate, and ethyl stearate) and a stabilizer (Tween-80) are included.

EXAMPLES

The following examples illustrate the present invention.

Example 1A — Ultraviolet Radiation

Two patients with overexposure to an ultraviolet lamp were seen. Both experienced localized severe skin hyperemia, erythemia, tenderness of the affected area, localized swelling (edema) and marked blanching of the surface on finger pressure. A single application of 25 mg/kg body weight of ethyl linoleate was applied topically by inunction. Within three minutes, there was virtually total reversal of all of the above symptoms.

Example 1B — Solar Radiation

Thirty-eight patients were treated following extensive exposure to solar irradiation. These patients all presented with marked cutaneous redness, hyperemia, hyperesthesia, heat, edema, and pressure-induced blanching. The area affected ranged from 5% body surface area to 80% body surface area. A single topical dose of 25 mg/kg body weight of ethyl linoleate was applied by inunction. Within 2.9 ± 0.4 minutes all of the above symptoms reversed. By 3 days following therapy, all patients exhibited increased melanin pigmentation without superficial keratin slough. Three patients who were taking antihistimine preparations at the time of their injury exhibited peeling (keratin slough).

Example 2 – Non-infectious Conjunctivitis

Four patients were seen with non-infectious conjunctivitis. The individuals ranged in age from 17 years through 42 years. Among the four patients, 6 eyeballs were involved. The lesion was caused by photoexposure (arc welding light) in one and by smoke in the remainder. The conjunctivae were markedly reddened, exudative, and excruciatingly painful. Both the lid and globar conjunctiva were involved in all instances. Within 3 minutes of the instillation of a single drop (6.7 mg) of ethyl linoleate into the eye, all signs and symptoms were relieved.

Example 3 — Hemorrhoids, Acute

Five patients were seen with acute hemorrhoidal inflammation. Patients ranged in age from 34 through 67 years of age. In all, one or more hemorrhoids were observed to be red, hyperemic, edematous, and exquisitely painful. A single application of two drops (13.4 mg) of ethyl linoleate by inunction was used in each case. Within 12 minutes (average) in all, all symptoms but hemorrhoidal protrusion had abated. Within 32 minutes, edema was resolved in all but one patient who retained a slight, protruding hemorrhoidal tag.

Example 4 — Abrasions

Twenty-two patients ranging in age from 6 years through 42 years of age were seen with abrasions. Abrasions involved the hands, arms, lower legs, and/or feet in all patients. Lesions exhibited loss of epidermis, redness, hyperemia, tenderness, and serum (and/or blood) exudation. There was a surrounding flare of hyperemic involvement in 90% of the lesions. Treatment comprised a single application of 1–5 drops (6.7–33.5 mg) ethyl linoleate by inunction. Within 0.5 – 5 minutes all symptoms and signs—with the exception of the loss of epithelium itself (i.e., healing)—were observed in all patients.

Example 5 — Ingrown Finger or Toenail (Granulation)

Eight patients, ranging in age from 6–43 years, were seen with ingrown nail with granulation beside the nail. Patients presented with markedly tender, heaped up, exudative, exquisitely tender granulations at the site of the ingrown nails. Treatment in all comprised the application daily of a single drop (6.7 mg) of ethyl linoleate dropwise to the lesion. In all, tenderness and redness abated by 7 minutes post-treatment. In all, edema, hyperemia, and the granulation tissue itself had abated by the fourth day.

Example 6 — Skin Graft Donor Sites

In 17 patients split-thickness skin grafts were removed from the back, arms, buttocks or thighs for the purpose of replacing skin losses elsewhere on the body. The patients' donor sites ranged in size from 12 to 200 square inches. (In the usual patient, the donor site is covered by a variety of gauze and/or medication dressings. In the usual patient, the area is markedly tender, red, and edematous.) In all patients, the thickness of skin donated was 0.008–0.013 inches. Two patients had pre-existing neurological disease such that the area of donor site was in a denervated zone. (In the usual case, such a lesion heals extraordinarily slowly an exhibits inflammation for a prolonged period of time.) Patients ranged in age from 18–67 years. Ethyl linoleate was applied dropwise, after which it was spread by inunction to the donor site. Sometimes the drug was applied immediately and sometimes it was applied after the donor site had been left exposed to the air for periods of time ranging from 15–60 minutes. During the period of air exposure, blood crusts formed on the surface. Ethyl linoleate was applied to this dried surface. In all patients, there was no pain, redness, edema, or stiffness of the donor site. In fact, 40% of the patients spontaneously inspected their extremities in an attempt to discover the area from which the skin had been removed. They indicated their complete absence of pain from the donor site.

Example 7 — Vaginitis

Two patients, 9 and 32 years old respectively, were seen with vaginitis (non-specific and Trichimonas, respectively). One exhibited pain, redness, and tenderness of the peri-vaginal and intra-vaginal region and one pain intra-vaginally and itching peri-vaginally. Treatment comprises application of ethyl linoleate by inunction, one only, to the affected mucous membrane and skin. All signs and symptoms abated within 4 minutes in each. The treatment did not reverse or abate the Trichimonas problem.

Example 8 — Poison Ivy

Nine patients, ranging in age from 6–67, were seen with poison ivy. Two of these patients had previously required Cortisone to prevent the poison ivy from becoming generalized over the skin (and in one, systemic). All patients presented with itching, red, raised, weeping papules typical of poison ivy. Treatment comprised the single topical application of 25 mg/kg ethyl linoleate by inunction. In all patients, itching ceased within 12 minutes, redness abated virtually immediately (by 0.5 minute), and the lesions began to dry within 24 hours. In no patient was there noted spread of the lesion to any other part.

Example 9 — Psoriasis

Three patients, ranging in age from 32–46 years, were seen with psoriasis of face, forehead, and/or back. The lesion had been intermittently present for an average of 11 years. It was manifest by silvery scaling, reddened elevating itching lesions in all patients. A daily topical application of 12.5 mg/kg body weight of ethyl linoleate was used in treatment. Ethyl linoleate was applied by inunction and was used from 5 days to 21 days. In all patients, all manifestations of the lesion had abated by five days from the initial therapy.

Example 10 — Herpes Simplex (Cold Sores, Aphthous Ulcers)

Seven patients, ranging in age from 8–61 years were seen with excrutiatingly painful yellowish-red ulcerated lesions of the oral mucous membrane or lip. The lesions were surrounded by a narrow zone of hyperemia and edema. Treatment comprised careful drying (with gauze) of the area and the application of a single drop (6.7 mg) of ethyl linoleate by dropwise to the lesion. Pain was relieved in all within 6 minutes of treatment; and the lesion was, subjectively and objectively, totally eradicated within 12 hours except in one patient. In this patient, who was concurrently on antihistaminic agents, the lesion of the lip, although without subjective symptoms, was objectively present for 48 hours.

Example 11 — Pruritis Ani/Cruri

Five patients, ranging in age from 4–65 years, were seen with redness, itching, exudation, and/or weeping of the area about the anus and/or in the periscrotal and perineal area. Treatment in each comprised a single dose of ethyl linoleate, 25 mg/kg body weight, by inunction. Within 8 minutes in all, complete reversal of objective and subjective signs and symptoms was observed.

Example 12 — Chemical Inflammation

Three patients were seen after contact of the tongue, lips, or arm with formol (1 patient) or phenol (2 patients). Lesions were red, hyperemic edematous and painful. Within 2.6 minutes of application of 1–3 drops ethyl linoleate by inunction, all signs and symptoms had abated.

Example 13 — Insect Stings/Bites

Seven patients were seen after contracting insect stings or bites. The patients ranged in age from 4–57 years of age. Offending agents comprised mosquito (two patients), wasps (two patients), bees (two patients), and bedbugs (one patient). Lesions comprised elevated, red, painful or itching papules with markedly reddened flare surrounding same. Treatment comprised a single topical application of one drop (6.7 mg) of ethyl linoleate by inunction. In all cases subjective and objective symptoms were alleviated within 3 minutes. Two of the patients exhibited systemic response in previous episodes of insect bite/sting; none exhibited these symptoms subsequent to ethyl linoleate.

I claim:

1. A method of treating an inflammatory response invoked by a chemical selected from one member of a group consisting of histamine, serotonin, and a prostaglandin in mammals which comprises topically applying to body surfaces of said mammals an inflammation-alleviating amount of ethyl-cis,cis (9,12)-octadecadienoate.

2. The method of claim 1 wherein the inflammation-alleviating amount of ethyl-cis,cis(9,12)-octadecadienoate is 0.2–0.8 mg/cm$^2$.

3. The method of claim 1 wherein the inflammation-alleviating amount of ethyl-cis,cis(9,12)-octadecadienoate is 0.5 mg/cm$^2$.

4. The method of claim 1 wherein the inflammation-alleviating amount of ethyl-cis,cis(9,12)-octadecadienoate is 15 mg/kg to 75 mg/kg of body weight of the mammal.

5. The method of claim 1 wherein the inflammation-alleviating amount of ethyl-cis,cis(9,12)-octadecadienoate is 25 mg/kg of body weight of the mammals.

6. The method of claim 1 wherein ethyl-cis,cis(9,12)-octadecadienoate is applied neat.

7. The method of claim 1 wherein there is applied an inflammation-alleviating amount of ethyl-cis,cis(9,12)-octadecadienoate and a lesser amount of a food grade antioxidant.

8. The method of claim 7 where said food grade antioxidant is selected from a member of the group consisting of α-tocopherol, d,l-histidine and tertiary butyl hydroquinone.

9. The method of claim 1 where the inflammatory response is associated with solar radiation.

10. The method of claim 1 were the inflammatory response is associated with hemorrhoids (acute).

11. The method of claim 1 where the inflammatory response is associated with abrasions.

12. The method of claim 1 where the inflammatory response is associated with vaginitis.

13. The method of claim 1 where the inflammatory response is associated with psoriasis.

* * * * *